United States Patent [19]
Beall et al.

[11] Patent Number: 6,029,520
[45] Date of Patent: Feb. 29, 2000

[54] ULTRASONIC MONITORING OF RESIN CURING IN A PRESS FOR THE PRODUCTION OF PARTICLE BOARD AND SIMILAR MATERIALS

[75] Inventors: Frank C. Beall, El Sobrante; Li-Heng Chen, Albany, both of Calif.

[73] Assignee: The Regents of the University of California

[21] Appl. No.: 09/169,834

[22] Filed: Oct. 9, 1998

[51] Int. Cl.⁷ .................................................. G01H 1/00
[52] U.S. Cl. ................... 73/579; 73/587; 73/590
[58] Field of Search .............................. 73/587, 590, 632, 73/579, 582, 588, 609, 610, 599; 162/49; 374/53

[56] References Cited

U.S. PATENT DOCUMENTS

H465   5/1988   Brown ........................ 73/590

*Primary Examiner*—Hezron Williams
*Assistant Examiner*—Thuy Vinh Tran
*Attorney, Agent, or Firm*—Allston L. Jones

[57] ABSTRACT

The technology used in the present invention is acousto-ultrasonics (AU), in which a transmitted signal, at a controlled frequency is injected into a specimen with one transducer and received at another location by another transducer, permitting evaluation of the condition of the material in the signal path. In the experiments that were made using the present invention, the material within the press was a particleboard mat having the signal injected into the edge of one platen and received at the edge of the second platen. The AU signal received at the second platen is initially in response to pressure changes in the mat and subsequently follows the progression of internal bonding of the material. Since the propagated wave through the mat reacts to resin curing during the last phase of pressing, changes in material or press variables are reflected directly in shifts of the curve received at the second platen. By monitoring the AU response curve, the press can be manually or automatically controlled to open within a specific range of board properties, such as IB. Not only does the technology of the present invention permit the shortest possible press cycle, it also permits control over the desired internal bond of the boards. The technology can be used in many types of presses and can serve as a supervisory system for press performance to determine if any openings are degrading in heat transfer. Additionally, shifts in the AU response curve can alert the press operator to both trends and abrupt changes as they occur.

32 Claims, 6 Drawing Sheets

ULTRASONIC MONITORING OF RESIN CURING IN A PRESS FOR THE PRODUCTION OF PARTICLE BOARD AND SIMILAR MATERIALS

FIELD OF THE INVENTION

The present invention relates to the curing process of resin bonded particles or layers during manufacture, more specifically to a positive way of monitoring the curing of such materials, while still in the press during the manufacturing process, and thus determine the optimum time for removing the product from the press. This invention can be applied generally to all types of wood composites, such as particleboard, oriented strandboard, chipboard, medium density fiberboard, insulation board, etc. It also could be used for laminated products, such as glued-laminated beams, laminated veneer lumber, plywood, and products having laminated surfaces.

BACKGROUND OF THE INVENTION

Wood-composite presses are open-loop controlled by a timed cycle that includes closing, pressing, and opening. The press time must be conservative to prevent "blows" in the press and to develop the degree of cure desired in the resin. Blows occur when the internal bond of the board is not sufficient to withstand the internal steam pressure when the press is opened. However, in the absence of a blow, if the press opening occurs too early, the board can have an unacceptably low internal bond (IB) from inadequate curing in the core. One well known means of determining the progression of curing is to monitor the core temperature of a board during pressing. This is usually conducted when conditions are changed or problems are suspected with a press opening, but is not useful as a continuous monitoring technique. However, the monitoring of the temperature of the core is, at best, a crude measure of the point of curing.

Several prior art techniques have been used to monitor the curing of adhesive bonds by using means sensitive to the properties of adhesives or physical quantities related to the chemical reactions during polymerization with varying degrees of success, or the lack thereof. Those prior art techniques fall into two broad categories: non-acoustic methods and ultrasonic methods.

The non-acoustic methods include a number of techniques that have been used for cure monitoring: dynamic mechanical analysis (DMA), differential scanning calorimetry (DSC), dielectric property analysis, infrared spectroscopy (IS), and pulsed nuclear magnetic resonance (PNMR). In DMA, a layer of polymer is vibrated to obtain the complex modulus of the material, which is then related to the changing viscoelastic properties of the polymer. This method does not take into account the interaction of the adhesive with adherend, specific specimen size and shape, and a thick layer that is greater than the thickness of normal adhesive bonds. DSC is used to study the heat of reaction of materials. While useful for developing kinetic information, DSC requires bulk curing and lacks sensitivity to non-thermal transitions. Dielectric property analysis involves measuring changes in an electric field by applying a voltage to capacitor plates contacting the material. Physical and chemical changes during curing reduce the freedom of movement of polar groups that attempt to align with the electric field, increasing the dissipation of the field energy. Similar to DMA, the dielectric method is sensitive to the solidification of the adhesive material (polymerization), but not all phases of adhesion. Infrared spectroscopy uses an optical fiber to measure infrared radiation associated with heat generated during an exothermal reaction. The limitation of the method is the large fiber diameter (0.12 mm) compared with the bond thickness (in the range of 0.1 mm), and sensitivity only to exothermic reactions. PNMR is one of the more sensitive methods for determining changes in viscosity, increases in degree of polymerization, and solid transitions. Further, it is very complementary to ultrasonic techniques. In summary, non-ultrasonic methods of cure monitoring can assess the solidification of the adhesive, but not all of the phases of bond curing, interaction with the adherend, or the final quality of the bond. Most of these methods apply to continuous layers thicker than normal adhesive bonds and are for laboratory use only. The advantage of non-ultrasonic methods is that they could complement acoustic methods by providing additional information on bond curing, independent of effects of the adherend.

Since the early 1950s the use of conventional ultrasonic methods to test adhesive bonds was explored with limited success using techniques such as through-transmission and pulse-echo at normal transmission to the bond plane. Recently, success in monitoring of curing has been achieved using more complex techniques, including interface waves, horizontal shear (SH) waves, and acousto-ultrasonics (AU), however, all suffer from serious limitations. Although these techniques indicate sensitivity to adhesive bond curing, they require a special arrangement of transducers and a geometry of specimens that is impractical for most industrial applications.

AU was originally developed as a means to assess flaw distribution and associated changes of the mechanical properties of fiber-reinforced composites. Recent research has also shown that AU can predict damage developed in composites, quality of adhesively-bonded joints, and material anisotropy. Because of the similarity between fiber-reinforced composites and wood, this method has also been applied to the evaluation of adhesive bonds in wood products, e.g., veneers, plywood, etc.

AU began as a combination of conventional ultrasonic testing (UT) and the sensitivity of AE (acoustic emission) transducers, in an attempt to measure changes in signal characteristics in highly attenuating materials, such as organic composites. Similar to ultrasonic through-transmission, an AU stress wave is injected into a material and the response is captured at another point of the specimen. However, the received signal was processed using methods similar to those used in AE, i.e., measuring various waveform parameters rather than reflections from discontinuities, as in UT. Efficiency of wave propagation is correlated with the physical properties of the material. Lower wave attenuation is associated with greater fracture resistance, absence of material defects, and higher overall strength. Unlike well defined wave paths, as in UT, the received AU signal is a result of multiple reflections, wave interactions, and mode changes.

Various means were also used to measure transmitted wave energy. In an early AU approach, signal energy was assessed using the "stress wave factor" (SWF), defined as a product of the pulse repetition rate, the reset time of the counter, and the number of positive slope crossings of the waveform over a preselected threshold. Since SWF depends on an arbitrarily set threshold, other means of measuring wave energy have since replaced the use of SWF. For example, RMS (root mean square) voltage and peak voltage are measurements independent of threshold level, and therefore give a more precise estimation of the signal energy. Increased availability and reduced costs of computers and A/D converters have permitted precise digitization of the signals and definition of many other signal features in the time and frequency domains, such as the area within time and frequency intervals, centroids, moments, peaks of frequency, and others.

From the short comings of all of the prior methods it is clear that the ideal technology to monitor the curing process in particleboard and similar products needs to be non-intrusive, inexpensive, reliable, and adaptable under automatic or manual press control for the desired state of operation. Fortunately, all of these characteristics are met by the present invention.

SUMMARY OF THE INVENTION

The technology used in the present invention is acousto-ultrasonics (AU), in which a transmitted signal, at a controlled frequency is injected into a specimen with one transducer and received at another location by another transducer, permitting evaluation of the condition of the material in the signal path. In the experiments that were made using the present invention, the material within the press was a particleboard mat having the signal injected into the edge of one platen and received at the edge of the second platen. The AU signal received at the second platen is initially in response to pressure changes in the mat and subsequently follows the progression of internal bonding of the material. Since the propagated wave through the mat reacts to resin curing during the last phase of pressing, changes in material or press variables are reflected directly in shifts of the curve received at the second platen. By monitoring the AU response curve, the press can be manually or automatically controlled to open within a specific range of board properties, such as IB. Not only does the technology of the present invention permit the shortest possible press cycle, it also permits control over the desired internal bond of the boards. The technology can be used in many types of presses and can serve as a supervisory system for press performance to determine if any openings are degrading in heat transfer. Additionally, shifts in the AU response curve can alert the press operator to both trends and abrupt changes as they occur.

BRIEF DESCRIPTION OF THE FIGURES

FIG. 6b illustrates the variation of core temperatures (° C.) for the boards in FIG. 6a.

FIG. 8b illustrates the variation of temperature (° C.) on AU transmission for boards in FIG. 8a.

DESCRIPTION OF THE PREFERRED EMBODIMENT

Figure 1:
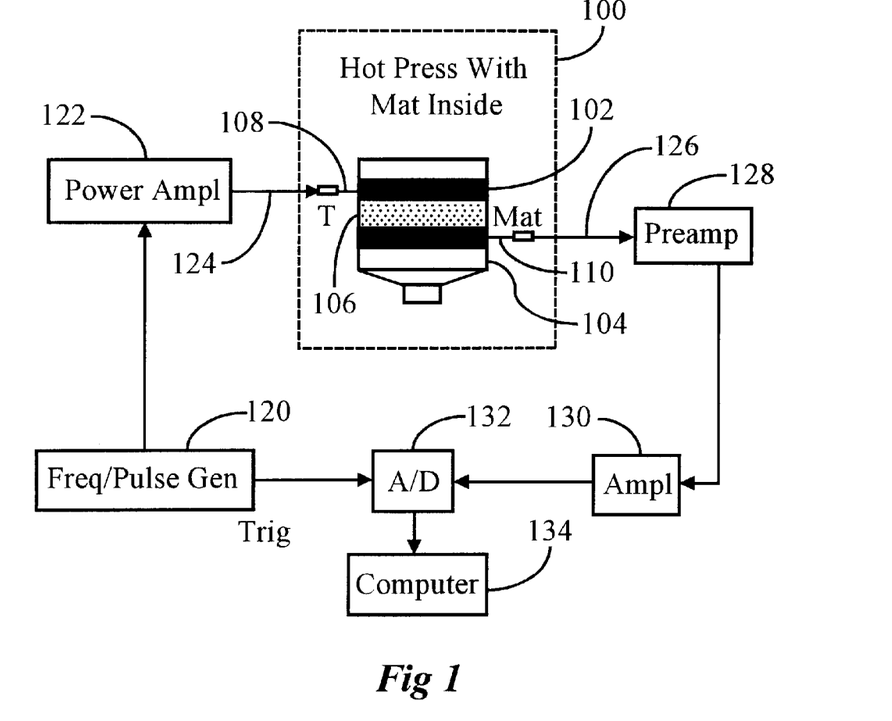
FIG. 1 is a schematic diagram of the system of the present invention for acousto-ultrasonically monitoring and controlling a press for the production of particleboard and similar materials.

FIG. 1 is a schematic diagram of an embodiment of the equipment necessary to implement the present invention with an AU system integrated with press 100. Press 100, in simplified form, includes a upper platen 102 and a lower platen 104 with the mat 106 being formed located between platens 102 and 104. Attached to the left side of upper platen 102 is a first waveguide 108, and attached to the right side of lower platen 104 is a second waveguide 110. In this diagram, first waveguide 108 has a transmit transducer T connected thereto and spaced apart from platen 102. Similarly, second waveguide 110 has a receive transducer R connected thereto and spaced apart from platen 104. Transmit transducer T converts an electrical signal that is applied thereto by power amplifier 122 (discussed more fully below) to an AU wave to pass through waveguide 108, platen 102, mat 106, platen 104 and waveguide 110 to receive transducer R where the received AU wave is converted into an electrical signal that is applied to preamplifier 128 which is discussed further below.

Given the high temperatures generated in a press of the type used to form particleboard and the like, waveguides 108 and 110 are typically constructed of stainless steel and screwed into threaded wells in platens 102 and 104, respectively. In addition, each waveguide is typically on the order of 200 mm in length to isolate transducers T and R from the high temperatures generated in press 100. Further, it is suggested that waveguides 108 and 110 be on opposite sides of press 100, as shown here, to minimize direct air coupling of the AU signal from transmit transducer T to receive transducer R attached to waveguide 110. By doing so, the AU signal received by transducer R will be more substantially the AU signal that has propagated through mat 106, thus limiting any additive effect of the pure transmit AU signal with the AU signal that has propagated through mat 106.

FIG. 1 additionally shows, in simplified form, the generation of the AU transmit signal for application to press 100 and the detection and processing of the AU received signal to determine the internal conditions of mat 106 at any point in time. Frequency/pulse generator 120 generates a series of bursts, with each burst containing a signal at a selected frequency (e.g., 60 kHz) which is then applied to power amplifier 122 to provide a signal strong enough to excite mat 106 with the amplified signal from power amplifier 122 being applied to transmit transducer T. Additionally, frequency/pulse generator 120 generates a trigger pulse at the begining of each burst which is applied to analog-to-digital (A/D) converter 132 to synchronize the transmission pulse with the received data being processed.

Figure 2:
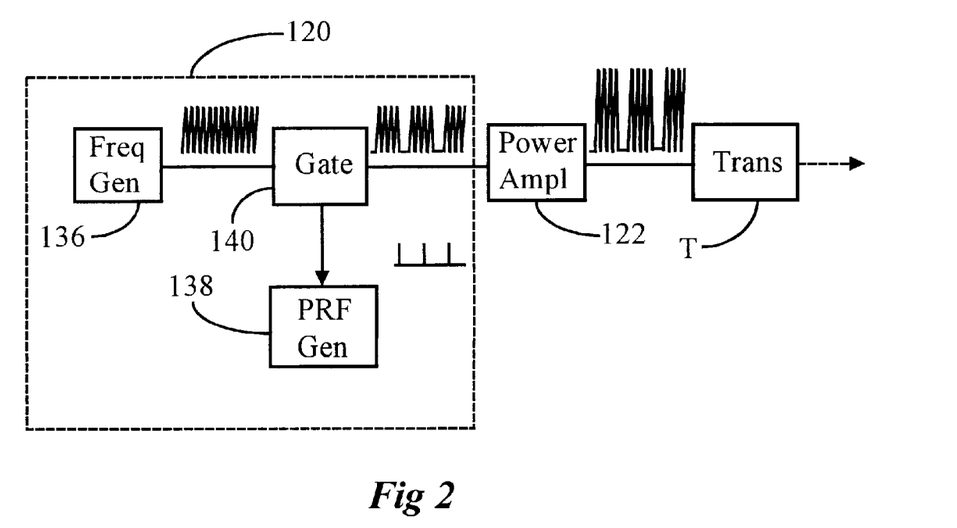
FIG. 2 is a more detailed schematic diagram of the AU tone-burst signal generation portion of the schematic of FIG. 1.

FIG. 2 more specifically illustrates the generation of the transmit signal of FIG. 1. Here the typical construction of frequency/pulse generator 120 is shown to consist of frequency generator 136 to generate a constant tone, continuous signal of a selected frequency (see waveform to right of Freq. Gen. 136) (e.g., Krohn-Hite 2200) that is applied to a high frequency gate 140. PRF (pulse repetition frequency) generator 138 (e.g., a pulse generator) provides evenly spaced trigger pulses (see waveform above and to right of PRF Gen. 138) to A/D 132 and gate 140 where the constant tone, continuous signal from frequency generator 136 is chopped into evenly spaced, constant duration signal bursts (see waveform to right of gate 140) (e.g., a sweep generator such as OK Electronics 204 to control the duration of the pulse bursts). The bursts from gate 140 are then applied to power amplifier 122 (e.g., Krohn-Hite 7500) to be amplified to the power level needed to excite press 100 and mat 106 (see waveform to right of power ampl. 122) and then to transducer T (e.g., piezoelectric transducer AET175L).

In the receive portion of FIG. 1, transducer R (e.g., piezoelectric transducer AET75L) receives the AU signal from mat 106 via platen 104 and waveguide 110, and converts that signal to an electronic signal for processing. The converted signal is then applied to preamplifier 128 (e.g., AET140B), followed by amplifier 130 (e.g., AET140B) to produce a signal that is strong enough to be further processed. From amplifier 130 the signal is applied to A/D 132 (e.g., AET140B) to be converted to a digital signal for processing by computer 134 (e.g., PC with 486 or better) where that signal is used to determine internal conditions of mat 106 (e.g., pressure and temperature) and to determine press opening data and otherwise control press 100.

Thus, in operation, the AU system of FIG. 1 begins with frequency/pulse generator 120 providing a tone burst output in the acousto-ultrasonic range (e.g., 60 kHz) with a repetition rate on the order of 50 Hz and a 333 $\mu$sec. tone-burst period (equivalent to a 0.2 duty cycle), which is amplified to match the characteristics of the transducer used (e.g., for the transducers listed above, 300 V p-p output). Additional items that might be used are: a 175 kHz resonant transducer as a pulser because of its high output over a range of tone-burst frequencies; and a 75 kHz receiver to maximize the output signal. The received signal can then be amplified as necessary. In the laboratory the received signal was amplified 60 dB (40 dB preamplification; 20 dB amplification), with a 30 kHz to 1 MHz bandpass amplification system. That amplified signal was then digitized at a sampling rate of 1 MHz for a period of 8192 $\mu$sec. and individual signals were sampled at 1 sec. intervals during pressing of mat 106.

To prove the present invention, a series of tests were run on a 610 by 610 mm laboratory press to evaluate the use of ultrasonic transmission to monitor the compression and curing of particleboard. The ultrasonic technique was acousto-ultrasonics (AU), in which a fixed frequency (60 kHz) was injected into one platen and the transmitted signal was received at the other. The variables considered were thickness from 10 to 30 mm, temperature from 120 to 200° C., and resin content from 2 to 10%. Urea-formaldehyde was used for the main study and phenol-formaldehyde for a preliminary one. The degree of resin curing was assessed by the amount of springback out of the press. The results reveal that AU provides a means of tracking the consolidation and curing of the mat, and reflected the impact of variables related to curing. All tests were conducted with hand-made particleboard in a single opening press with a target board density of 650 kg/m$^3$.

Board Fabrication and Formation.

The particleboard furnish was obtained from a Georgia Pacific mill. To minimize variation within the mat, only core furnish was used, with particles passing a 1.5 by 13 mm screen, having a species mixture of white fir (20%), Douglas-fir (20%) and pine (60%). On receipt, the furnish was stored at 6% EMC (equilibrium moisture content). Most of the study was conducted with urea-formaldehyde resin (GP3635) having a latent catalyst, which was stored at 5°. One preliminary test was run with phenol-formaldehyde resin (GP70CR66). The mat was blended using a laboratory rotary drum with a atomizing nozzle that produced a flat spray pattern. The furnish moisture content after storage was 7∓0.5%; after blending was 10∓2%. The mat was precompressed by hand and transported to the press using a 5-mm-thick aluminum caul. In order to monitor the mat temperature, type T thermocouples were placed at the center and at the surface 100 mm in from the edge of the mat. The mat was pressed in a single-opening, Williams, White & Company hydraulic press, having a maximum pressure of 15.5 MPa (Mega Pascals). The platens were 610×610 mm and were oil-heated using a Sterling 6016 circulating unit. One Schaevitz LVDT was located on an edge to monitor board thickness. The press was positioned-controlled using a PC-based computer that was also used for data acquisition and processing.

Preliminary Studies.

A feasibility study was made to demonstrate the overall response of AU to resin curing. This was done using 6% PF resin in one set of specimens and no resin, but the mass equivalent of particles in another set. The runs were made at 200° C. with a target thickness of 20 mm and density of 650 kg/m$^3$.

Following this, an expanded study was made to determine the amount of springback after pressing as a means of assessing the degree of cure at removal of the board from the press. This study was done with a single set of variables, namely:

Press temperature: 160° C.

Thickness: 20 mm

Resin content: 6%

Thickness and resin content were selected as nominal for commercial particleboard; the temperature was lower than commercial practice, but was chosen to extend the curing period sufficiently to generate more data on the degree of curing. A series of runs were made with boards removed at: 15 sec. intervals in the time range of 240–390 sec.; 30 sec. intervals in the time range of 390–420 sec.; and 60 sec. intervals in the time range of 420–600 sec. One board was produced at each time interval. The boards were forced-air cooled and stored at 20° C. and 12% EMC before being sectioned for springback measurements. Each board was cut into fifty 50×50 mm specimens.

Main Study.

On completion of the 160° C. springback testing, the study was expanded with the following variables (those in bold were from the preliminary study):

Press temperature (° C.): 120, 140, 160, 180

Thickness (mm): 10, 15, 20, 25, 30

Resin content (%): 2, 4, 6, 8

The range of variables was selected for extremes to understand the influence on ultrasonic transmission and was not intended to reflect commercial practices. The target density continued to be 650 kg/m$^3$ and the same core furnish and resin as for the 160° C. preliminary study. The runs were made in duplicate.

Results and Discussion

In the results, the output of a single AU parameter, RMS (root mean square), will be demonstrated. RMS output is essentially an expression of energy and is given by the expression:

$$RMS=[\Delta t^{-1}\int V^2(t)dt]^{0.5}$$

where Δt is the range of the measurement over time and V is the peak voltage.

Preliminary Tests.

Figure 3:
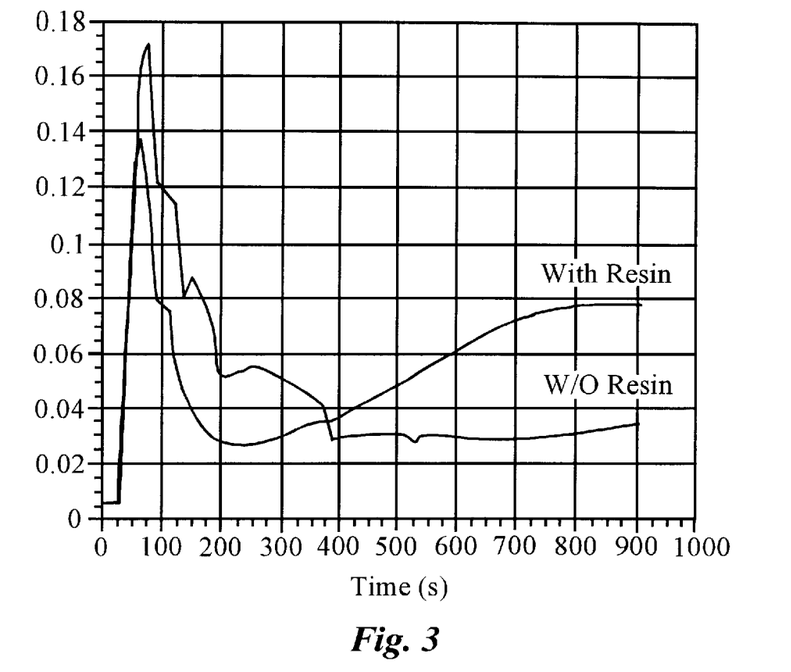
FIG. 3 is a comparison of AU transmission through particleboard with and without phenolic resin during the preliminary experiments.

FIG. 3 shows the results of the initial feasibility study on PF resin, which was used to advantage of the relatively long cure time as compared with UF. Both curves go through peaks of RMS output at the highest pressure on the mat, rapidly declining as the mat consolidates. The variations in the pressure and AU curve are a result of the inability to control small changes in the pressure. The "with resin" curve shows much more rapid consolidation, whereas the "without resin" cure is very erratic. At about 200 sec., the AU output of the normal "with resin" mat reaches a minimum and then at about 270 sec., begins increasing. No such increase occurred with the "w/o resin" mat, which was essentially constant after 380 sec. In the tests with UF resin, springback after pressing was used to confirm curing.

Figure 4:
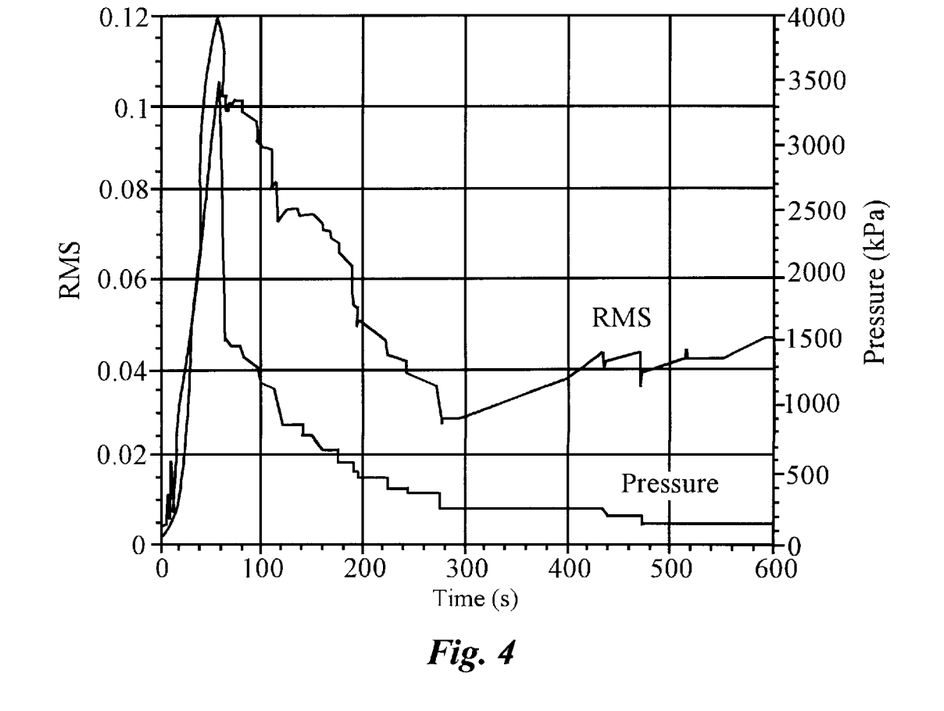
FIG. 4 compares the AU RMS response and pressure variations in a mat with urea resin during preliminary experiments.

FIG. 4 shows a typical unsmoothed curve from the 160° C. runs. Superposed on this curve is the pressure sequence in response to the PC program. Note that the "pressure" curve is similar to that of the "w/o resin" board in FIG. 3.

Figure 5:
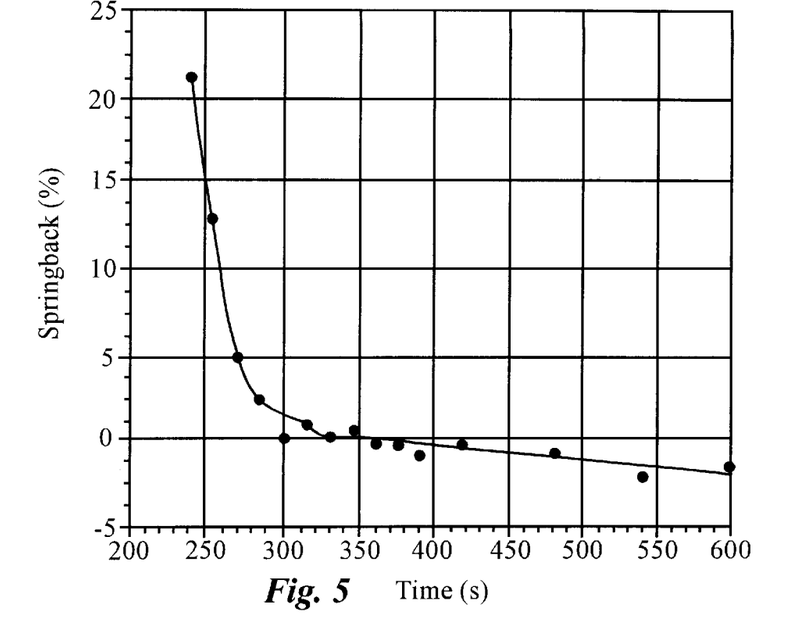
FIG. 5 illustrates springback for panels fabricated under conditions given for FIG. 4 during preliminary experiments.

FIG. 5 is also for the preliminary experiments and shows that springback declines exponentially to about 300 sec. and then fairly linearly beyond that point in time. Based on this data, it can be seen that adequate curing did not occur until about 30 sec. beyond the AU minimum by comparison with FIG. 4.

Main Study.

Figure 6A:
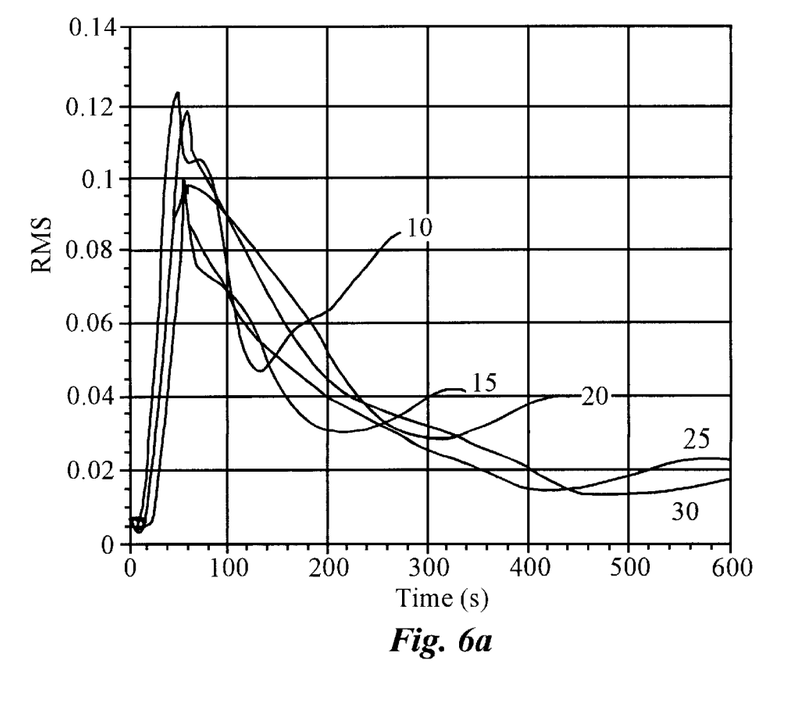
FIG. 6a illustrates the effect of board thickness (mm) on AU transmission for boards cured at 160° C. and 6% urea resin content.

The effect of thickness, press temperature, and resin content were studied at this point. The effect of thickness on AU output is shown in FIG. 6a and the corresponding core temperatures of the mats in FIG. 6b each for the thickness of board in mm indicated adjacent each curve in each of these figures.

Figure 6B:
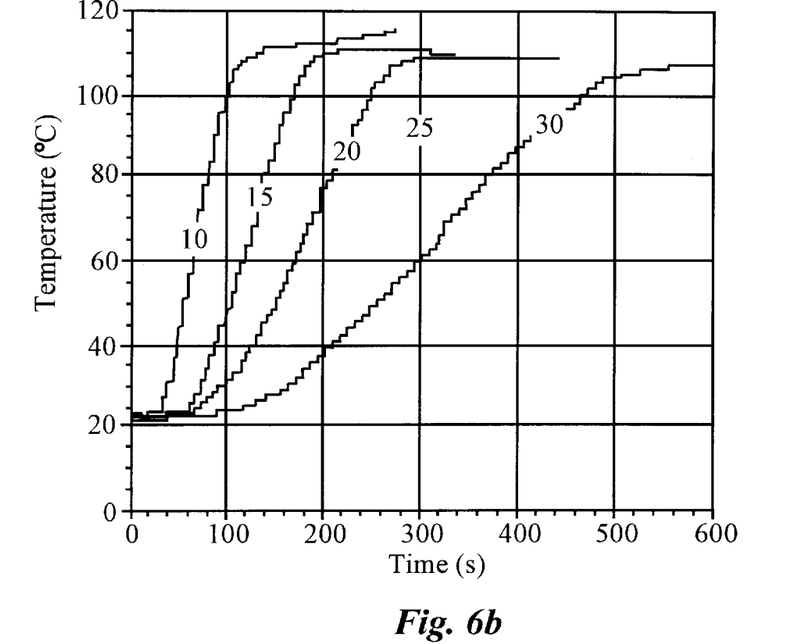

Using an AU-plateau criterion for determining the completion of cure, the corresponding cured times followed a linear relationship with thickness (y=35.5+20.9×), where the time increased 21 sec. for each millimeter of thickness. Note that both the AU and temperature curves are difficult to interpret for the cure point of the 30-mm sequence. The effect of mat thickness is to increase the ultrasonic attenuation, which could be overcome by higher input power and/or higher system gain.

Figure 7:
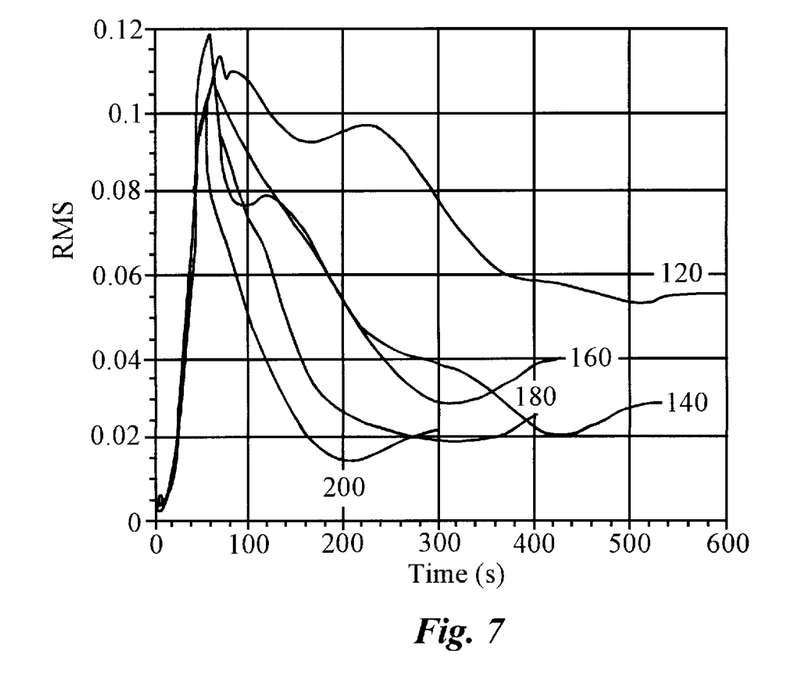
FIG. 7 illustrates the effect of temperature (° C.) on AU transmission for boards of 20 mm thickness and 6% phenolic resin content.

The predictability of AU for the curing condition over a temperature range of 120 to 200° C. is given in FIG. 7 (each curve is labeled with the corresponding temperature, 120, 140, 160, 180 and 200), with the acceptable curing point estimated at about 30 sec. after the minimum in the RMS curve. These results are similar to the effects of thickness, where the lowest temperature has similar ambiguity as the thickest board. Ultrasound is attenuated by increasing temperature of materials, however, that change is obscured by other variables in this case.

Figure 8A:
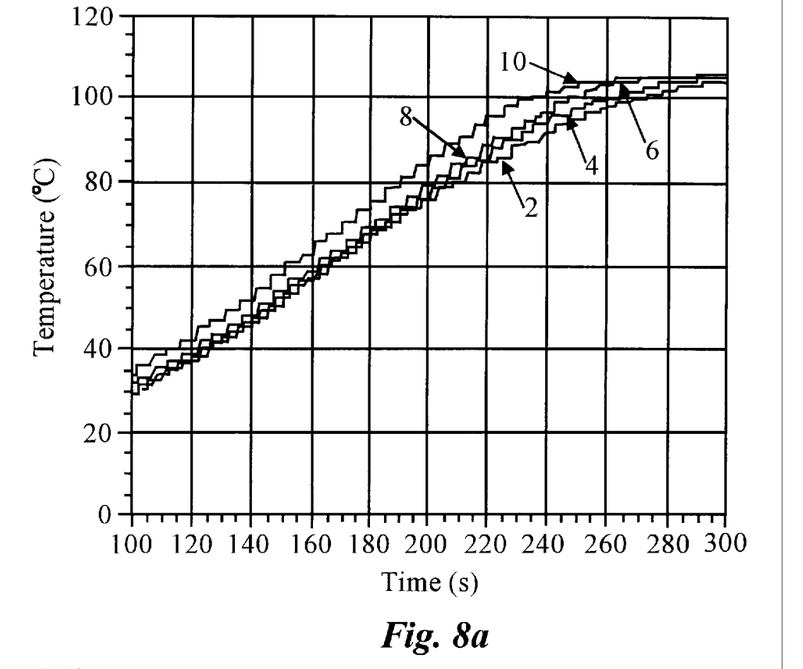
FIG. 8a illustrates the effect of resin content (%) on AU transmission for boards of 20 mm thickness, pressed at 160° C.
Figure 8B:
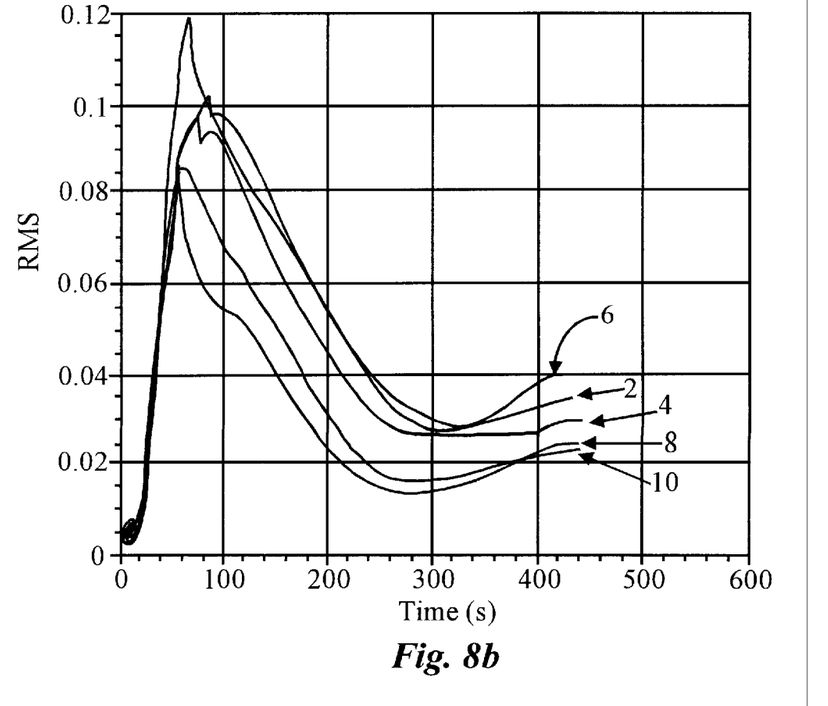

Perhaps the most interesting departure of results occurred with the variation in resin content from 2 to 10% as shown in FIGS. 8a and b wherein each curve is marked with the correspond resin content percentage. The temperature curves (FIG. 8a) are very close together, with a total spread of about 40 sec. from 2 to 10% resin content. However, this spread could have been from the change in moisture content of about 4% over this range. The RMS output (FIG. 8b) reflects the differences in the mat composition for each of the resin contents. A greater relaxation of the mat is evident with increasing resin content (and moisture content), but the cure point appears to be in the same narrow range as shown in FIG. 8a. The water of condensation could also be adding to the apparent delay in curing.

From the experimental results discussed above and shown graphically in the various figures the results support the conclusion that acousto-ultrasonics through transmission during pressing can be used to monitor the consolidation of the mat as well as the curing process for wood-based composites. In particular, it was shown that:

1. The use of waveguides inserted into the platens provides an effective means of injecting and receiving the AU signals without intruding in the pressing process;
2. The increase of AU output after the minimum corresponds to the curing period of the resin; and
3. Changes in thickness, resin content, and temperature cause shifts in the AU output that are related to resin curing.

The output signal from the transducer is affected by a number of key variables, including the development of strength of the mat (modulus); the attenuation of ultrasound from the presence of moisture and steam, and the temperature of the mat; and the acoustic coupling between the platens and mat. Some of these effects vary with the depth into the mat (platen to platen), but the level of energy transmission tends to be controlled by the weakest location in depth (mat thickness). Since transmission is measured through the entire thickness, there is no convenient method to differentiate the separation contributions to variability, and therefore these are lumped effects that change the level of ultrasonic transmission. It is also well-known that wood-composites in the press cure non-uniformly across the area of the mat. When all of these factors are considered, we can model the ultrasonic output by the following equation:

$$T_i = f(k_i, A_i, E_i)$$

where $T_i$=AU transmission at point i over the time of pressing $k_i$=coupling coefficient=f(p,s), where p=pressure at the surface and s=surface roughness $A_i$=attenuation coefficient=f($A_m$, T, t), where $A_m$=material coefficient, T=temperature, and t=material thickness $E_i$=modulus of material=f($r_c$, $r_t$, $r_b$, b), where $r_c$=resin content, $r_t$=resin type, $r_b$=resin bonding, and b=particle layering, geometry, etc.

$T_t$ is the output described in the curves of RMS vs time, and is the cumulative effect of the transmission over the full area of the mat as affected by the variables described above. Values of T can be used to determine the point at which the mat is sufficiently cured for the intended purpose. For example, this point can be a fixed time period after the minimum of the RMS curve, a specific RMS level after the minimum, or when the RMS reaches a plateau of essentially zero slope.

In terms of mat (or board) properties, the most important variable in the equation is the modulus (E). The most conventional means of determining the modulus in wood composite panels is to test them destructively by tension perpendicular, referred as an internal bond test. In this test, specimens of 50 by 50 mm in area are bonded to like-size blocks that can be pulled in tension to determine the load at failure. The internal bond, therefore, is a reasonable measure of the strength (or modulus) of the board.

Figure 9:
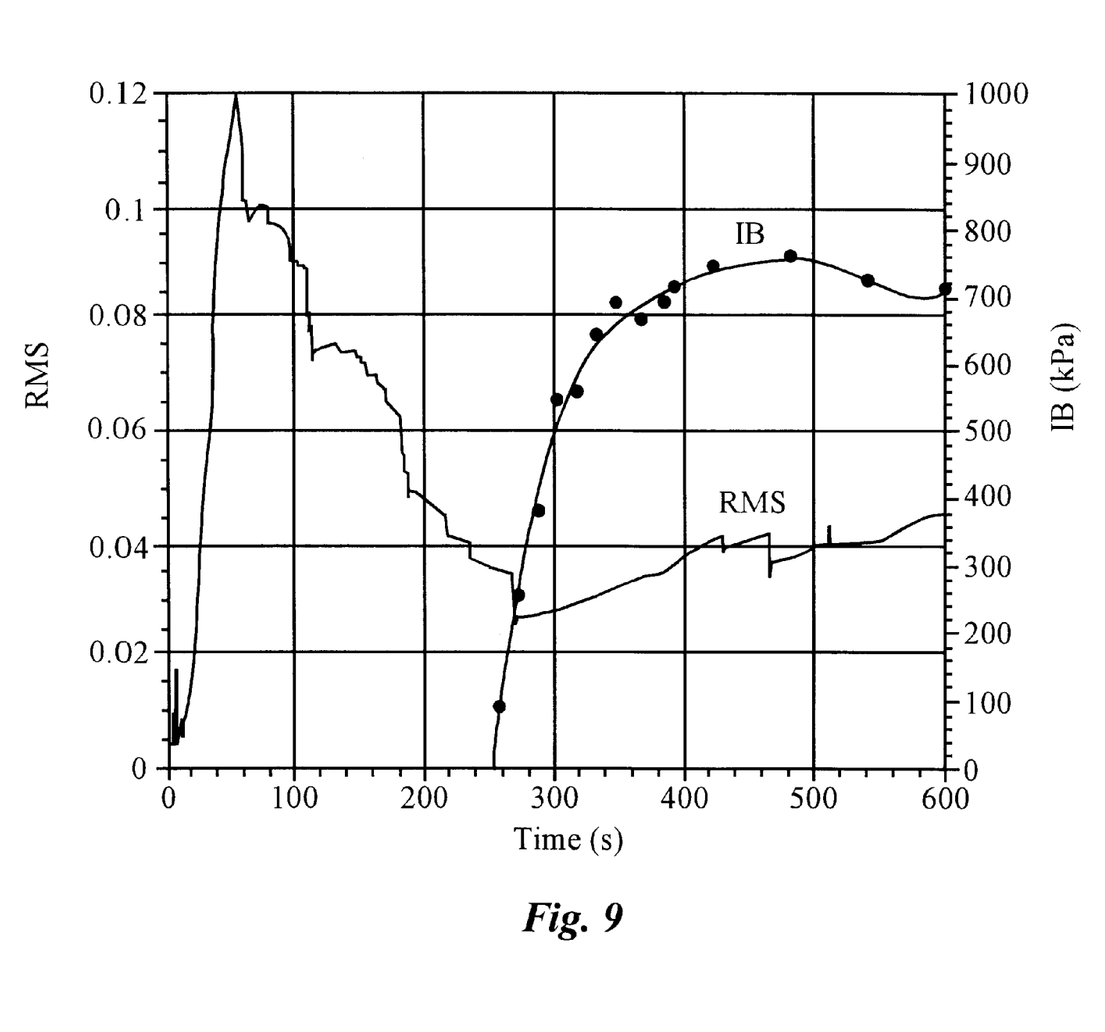
FIG. 9 shows a typical received RMS AU curve for particleboards produced with the same starting parameters as compared to the IB (internal bond) within 14 different sample boards that were removed from the press at various times after the typical minimum RMS value for the board being produced.

FIG. 9 shows two curves with a common time axis along the horizontal. One curve is a typical received RMS AU curve for 14 samples that were made to have substantially the same characteristics. The second curve is an extrapolated IB curve with the 14 different points thereon being the IB of the 14 different samples removed from the press at 14 different times after the minimum RMS value was reached. Therefore, it is clearly shown by FIG. 9 that the measure of the received RMS AU signal is an excellent measure of the development of average internal bond while that board is still in the press. Thus, it is possible for a user to make a trial run using the materials at hand for the products to be produced and determine the point on the RMS curve that corresponds to the desired properties of the final product, and then use that RMS value plus or minus a selected tolerance for variations in material to fully automate the process. Alternatively, the operator could use that trial run number to look for a similar response at or about the same point in time as a guide as to when the product is finished and can be released from the press.

While the focus of the discussion above has been to a laboratory press since that is the type of press that the experiments were conducted on, the method discovered and to which this writing is directed applies equally to all batch press, single or multi-opening, and continuous presses as well. For multi-opening presses, one or more openings can be monitored, and two openings can be monitored with a single transmitter and two receivers at the platens above and below the transmitter. In such a set-up, each response can be monitored individually to monitor the cure in two different major directions through the mat, or the two resulting signals can be added and handled as discussed above where there was only one receiver.

While the discussion above has been predominately directed to particleboard which was the focus of the experiments conducted, the present invention is by no means limited to particleboard. This invention can be applied generally to all types of wood composites, such as particleboard, oriented strandboard, chipboard, medium density fiberboard, insulation board, etc. It also could be used for laminated products, such as glued-laminated beams, laminated veneer lumber, plywood, and products having laminated surfaces. Thus, the present invention is not to be viewed only with particleboard in mind, but to all composite and laminated product which rely on a small amount of resin to bind the various portions of the product together. Thus the scope of the present invention is only to be limited by the scope of the claims appended hereto.

What is claimed is:

1. A method for monitoring the curing of a wood based composite mat of selected materials, including resin, into a resin bonded product while that mat is being formed in a press having a first platen and second platen with said mat located between said first and second platens during said curing, the method comprising:
 a. applying a plurality of acousto-ultrasonic multiple pulse bursts to said first platen of said press to excite said mat between said first and second platens;
 b. detecting, at said second platen of said press, a plurality of acousto-ultrasonic waves that have propagated through said mat to said second platen corresponding to said plurality of pulse bursts of step a;
 c. combining said plurality of acousto-ultrasonic waves detected at said second platen in step b into a selected waveform type; and
 d. monitoring said selected waveform of step c for a particular characteristic of interest that is related to a desired quality of said mat in the finished state.

2. The method as in claim 1 wherein said selected waveform type of step c is the RMS value curve of said selected waveform.

3. The method as in claim 2 wherein:
 during curing of said mat, said RMS value curve rises to a peak value and then decreases in value; and
 said particular characteristic of interest of step d is a selected point on said RMS value curve following said peak value.

4. The method as in claim 3 wherein said selected point is where said RMS value curve attains a zero slope.

5. The method as in claim 3 wherein said selected point occurs a selected period of time following a point where that said RMS value curve attains a zero slope.

6. The method as in claim 3 wherein said selected point is where said RMS value curve attains a selected level following a point of zero slope.

7. The method as in claim 1 wherein said plurality of acousto-ultrasonic multiple pulse bursts of step a are generated by a transducer having applied thereto an electrical signal consisting of a plurality of tone bursts each having a selected frequency, a selected duration and a selected repetition rate.

8. The method as in claim 7 wherein said selected frequency is 60 kHz.

9. The method as in claim 8 wherein said selected duration of each tone burst signal is 333 μsec.

10. The method as in claim 9 wherein said selected repetition rate is 50 Hz.

11. The method as in claim 1 further comprising the step of:
 e. removing said mat from said press in response to step c following the achievement of said particular signal characteristic.

12. The method as in claim 11 wherein said selected waveform type of step c is the RMS value curve of said selected waveform.

13. The method as in claim 12 wherein:
 during curing of said mat, said RMS value curve rises to a peak value and then decreases in value; and
 said particular characteristic of interest of step d is a selected point on said RMS value curve following said peak value.

14. The method as in claim 13 wherein said selected point is where said RMS value curve attains a zero slope.

15. The method as in claim 13 wherein said selected point occurs at a selected period of time following a point where that said RMS value curve attains a zero slope.

16. The method as in claim 13 wherein said selected point where said RMS value curve attains a selected level following a point of zero slope.

17. The method as in claim 11 wherein said plurality of acousto-ultrasonic multiple pulse bursts of step a are generated by a transducer having applied thereto an electrical signal consisting of a plurality of tone bursts each having a selected frequency, a selected duration and a selected repetition rate.

18. The method as in claim 17 wherein said selected frequency is 60 kHz.

19. The method as in claim 18 wherein said selected duration of each tone burst signal is 333 μsec.

20. The method as in claim 19 wherein said selected repetition rate is 50 Hz.

21. An apparatus to monitor the curing of a wood based composite mat of selected materials, including resin, into a resin bonded product, comprising:
 a press having a first platen and second platen disposed to receive said mat between said first and second platens for curing;
 an acousto-ultrasonic transducer coupled to said first platen to apply a plurality of acousto-ultrasonic multiple pulse burst waves to said first platen to excite said mat when placed between said first and second platens;

an acousto-ultrasonic receiver coupled to said second platen to detect each acousto-ultrasonic wave that propagates through said mat, when in place, from said first platen with each received acousto-ultrasonic wave corresponding to each of said plurality of acousto-ultrasonic multiple pulse burst waves applied to said first platen by said transducer and to generate a received electrical signal corresponding to said received acousto-ultrasonic waves;

a converter coupled to said acousto-ultrasonic receiver to transform said received electrical signal into a selected signal type; and a computer coupled to said converter to monitor said selected signal type of said received electrical signal for a particular characteristic of interest that is related to a desired quality of said mat in the finished state.

22. The apparatus of claim 21:

further including a frequency pulse generator coupled to said acousto-ultrasonic transducer to generate an controlling electrical signal having a plurality of multiple pulse bursts to be applied to said transducer; and wherein said acousto-ultrasonic transducer converts said controlling electrical signal into said plurality of acousto-ultrasonic multiple pulse burst waves.

23. The apparatus of claim 22 wherein said frequency pulse generator includes:

a frequency generator to generate a constant tone electrical signal of a selected frequency;

a pulse repetition frequency generator to generate trigger pulses at a selected repetition rate;

a high frequency gate coupled to said frequency generator and said pulse repetition frequency generator with said high frequency gate opening upon receipt of each trigger pulse to output a multiple pulse burst signal of said selected frequency for a selected period of time; and an amplifier coupled to said high frequency gate to amplify each multiple pulse burst signal.

24. The apparatus of claim 23 wherein said pulse repetition frequency generator is further coupled to said computer to apply said trigger pulses to said computer to synchronize said transmitted acousto-ultrasonic multiple pulse burst waves with said received acousto-ultrasonic waves.

25. The apparatus of claim 23 wherein said selected frequency is 60 kHz.

26. The apparatus of claim 23 wherein said selected duration of each tone burst signal is 333 $\mu$sec.

27. The apparatus of claim 23 wherein said selected repetition rate is 50 Hz.

28. The apparatus of claim 21 wherein said selected waveform type is the RMS value curve of said selected waveform.

29. The method as in claim 28 wherein:

during curing of said mat, said RMS value curve rises to a peak value and then decreases in value; and said particular characteristic of interest is a selected point on said RMS value curve following said peak value.

30. The method as in claim 29 wherein said selected point is where said RMS value curve attains a zero slope.

31. The method as in claim 29 wherein said selected point on is occurs at a selected period of time following a point where that said RMS value curve attains a zero slope.

32. The method as in claim 29 wherein said selected point on is where said RMS value curve attains a selected level following a point of zero slope.

* * * * *